(12) United States Patent
Le Comte et al.

(10) Patent No.: US 7,858,032 B2
(45) Date of Patent: Dec. 28, 2010

(54) DEVICE FOR SUPPLYING BLOOD TUBES TO A WHOLE BLOOD ANALYSER

(75) Inventors: Roger Le Comte, Perols (FR); François Dupoteau, Paris (FR)

(73) Assignee: Horiba ABX SAS, Montpellier (FR)

( * ) Notice: Subject to any disclaimer, the term of this patent is extended or adjusted under 35 U.S.C. 154(b) by 1022 days.

(21) Appl. No.: 10/592,708

(22) PCT Filed: Mar. 11, 2005

(86) PCT No.: PCT/FR2005/000595

§ 371 (c)(1),
(2), (4) Date: Jan. 11, 2007

(87) PCT Pub. No.: WO2005/101025

PCT Pub. Date: Oct. 27, 2005

(65) Prior Publication Data

US 2008/0318306 A1    Dec. 25, 2008

(30) Foreign Application Priority Data

Mar. 16, 2004 (FR) .................................. 04 02687

(51) Int. Cl.
*G01N 35/10* (2006.01)
(52) U.S. Cl. .............................. 422/65; 422/63; 436/47; 436/48; 436/49
(58) Field of Classification Search .................. None
See application file for complete search history.

(56) References Cited

U.S. PATENT DOCUMENTS

| | | | |
|---|---|---|---|
| 4,039,288 A | 8/1977 | Moran | |
| 4,475,411 A | 10/1984 | Wellerfors | |
| 4,518,264 A * | 5/1985 | Nohso | ........................ 366/208 |
| 4,609,017 A | 9/1986 | Coulter et al. | |
| 4,797,258 A | 1/1989 | Mochida | |
| 4,944,924 A | 7/1990 | Mawhirt et al. | |
| 5,224,585 A | 7/1993 | Blanco et al. | |
| 5,232,081 A | 8/1993 | Kanamori | |
| 5,286,959 A | 2/1994 | Demachi | |
| 5,366,062 A | 11/1994 | Markin et al. | |
| 5,380,488 A | 1/1995 | Wakatake | |
| 5,582,795 A | 12/1996 | Nishina et al. | |
| 5,623,415 A | 4/1997 | O'Bryan et al. | |
| 5,941,366 A | 8/1999 | Quinlan et al. | |
| 6,081,326 A | 6/2000 | Rousseau et al. | |
| 6,358,471 B1 | 3/2002 | Ishihara | |
| 6,374,989 B1 | 4/2002 | van Dyke, Jr. et al. | |
| 6,689,318 B1 | 2/2004 | Spork et al. | |

(Continued)

FOREIGN PATENT DOCUMENTS

CN    1334453 A    2/2002

(Continued)

*Primary Examiner*—P. Kathryn Wright
(74) *Attorney, Agent, or Firm*—Oblon, Spivak, McClelland, Maier & Neustadt, L.L.P.

(57) ABSTRACT

A device including a pre-analytical module provided with at least one tube stirrer for homogenizing blood and preventing clot formation and disposed on a line for single-tube transfer between an area for storing analyzable tubes, and at least one unitary operating whole blood analyzer and automatic tube-loading/unloading device arranged between the tube stirrer and the single-tube transfer line. The device is suitable for blood analyzers.

15 Claims, 6 Drawing Sheets

U.S. PATENT DOCUMENTS

| | | | |
|---|---|---|---|
| 7,678,331 B2 * | 3/2010 | Shanafelter | 422/65 |
| 2002/0021983 A1 | 2/2002 | Le Comte et al. | |
| 2002/0100806 A1 | 8/2002 | Harrop | |
| 2002/0155031 A1 * | 10/2002 | Itoh | 422/73 |
| 2003/0029254 A1 * | 2/2003 | Hvidtfeldt et al. | 73/863.33 |
| 2004/0022682 A1 | 2/2004 | Itoh | |
| 2005/0180884 A1 * | 8/2005 | Itoh | 422/63 |
| 2006/0081539 A1 * | 4/2006 | Safar et al. | 210/695 |
| 2007/0048185 A1 * | 3/2007 | Dupoteau et al. | 422/68.1 |
| 2007/0189926 A1 * | 8/2007 | Le Comte | 422/65 |
| 2007/0217951 A1 * | 9/2007 | Matsumoto | 422/67 |
| 2009/0142844 A1 * | 6/2009 | Le Comte | 436/8 |

FOREIGN PATENT DOCUMENTS

| | | | |
|---|---|---|---|
| EP | 0 061 317 A1 | | 9/1982 |
| EP | 0 275 119 | | 7/1988 |
| EP | 0 295 048 | | 12/1988 |
| FR | 2 812 088 A1 | | 1/2002 |
| FR | 2859285 | * | 3/2005 |
| JP | 2004-37320 | | 2/2004 |
| WO | 95/03548 | | 2/1995 |
| WO | WO 98/01760 | | 1/1998 |
| WO | WO2005/101024 | * | 10/2005 |

* cited by examiner

DEVICE FOR SUPPLYING BLOOD TUBES TO A WHOLE BLOOD ANALYSER

The invention relates to a device for supplying tubes of blood to whole blood analysers.

BACKGROUND OF THE INVENTION

I. Field of the Invention

Whole blood analysers are analysers which carry out analyses on tubes of blood containing all the elements of the blood, in contrast to analysers which work on blood plasma or serum.

II. Description of Related Art

In contrast to the analyses carried out on blood plasma or serum the blood which is to be analysed by a whole blood analyser has to be carefully mixed a very short time before the analysis. This agitation phase is absolutely necessary in order to homogenise the blood so as to re-suspend the cells which naturally settle out when the tube is motionless, and it has to be carried out in accordance with the recommendations of the standardisation committees.

This agitation phase is treated differently depending on the type of analyser used and its degree of automation. In the simplest analysers there are no agitation means in the apparatus and the agitation then has to be carried out manually by the operator prior to the analysis.

In more sophisticated analysers, and particularly in haematology equipment, the tubes are installed before analysis in agitators made up of wheels or racks.

In agitators provided with wheels the tubes of blood are placed in indentations arranged around the periphery of a wheel. Each tube is then inverted and returned to its initial position on each revolution of the wheel. The quality of the agitation is good but the automation is limited to the capacity of the wheel, which has to be changed each time capacity is reached.

In agitators provided with racks, the tubes are placed in racks before being loaded into an analyser. The analyser then arranges for the agitation of the tubes followed by the analysis and storage of the analysed racks.

In order to increase the yield and efficacy of the analyses, it is normal to add automatic conveyor belts to the analysers for carrying the tubes which are to be analysed from a storage zone to the point of analysis where they are taken over by the analyser.

The majority of automated lines use a rack-type conveying method with passing means also operating with racks. This technique is used particularly by the company Sysmex, which markets a system in which the racks are mounted on a rail which carries them from one analyser to the other, the passage to an analyser being carried out in a translatory movement. The storage and flow management of the racks are carried out by a buffer storage system. A description of this technique can be found in U.S. Pat. No. 5,232,081. The storage and flow management of the racks are provided by a storage apparatus which makes it possible to adapt the movement of a rack in the storage system on the conveyor to the analysing sequence. The racks have proved effective for analyses which do not require a second passage into the analyser, as they make it possible to achieve high analysis rates. However, this system lacks flexibility if for any reason a tube has to be fed into the analyser a second time. In this case the entire rack containing the tube in question has to be returned to the storage device in order to be sent back into the analyser.

The use of racks in an automated line also requires restrictive arrangements in terms of changes of direction and turns required of the conveyor belt. Examples of solutions which set out to solve these problems are described in particular in U.S. Pat. No. 5,366,062 and U.S. Pat. No. 5,380,488.

Another problem concerns reading the information written on the label of each of the tubes, owing to the fact that the automated line has to have readers for reading the labels on each tube through the rack. A number of technical solutions have been proposed for solving this problem. Thus, for example, U.S. Pat. No. 6,081,326 and U.S. Pat. No. 5,286,959 describe a device for rotating the tube on itself inside the rack in order to position its label in front of an optical reader positioned in front of a slot in the rack. According to another embodiment described in US Patent Application 2002/0100806, a lug located in the indentation containing the tube enables the label on the tube to be positioned in front of a window in the rack to allow an optical reader to read the contents of the label. These patents clearly show the complexity and difficulty in reading a label on a tube stored in a rack.

Moreover, the use of racks in an automated line has its limits when there is a need to manipulate or select a specific tube in order to run a new series of tests on it. The diagnosis and new measuring techniques show that a tube must be capable of being re-tested or undergoing a new series of tests after a first disputed analysis. In this context the automated line using racks is of no value and the use of an automated line with a mono-tube support appears to be better suited to the needs of modern laboratories.

Automated lines with a mono-tube support in the majority of cases are lines comprising conveyor belts. Descriptions of this type of line are to be found in U.S. Pat. Nos. 6,374,989 and 5,941,366. In U.S. Pat. No. 5,224,585, the conveyor belt is used as a magnetic support enabling the supports to remain adhered to the belt during both horizontal and vertical movements.

In the field of automated lines, and particularly for biochemical apparatus, chaining techniques are also used. However, the reaction times of these apparatus are quite long. A complex chaining system which combines a tube support with a receptacle integrally attached to the chain and allowing a chemical reaction to be carried is described in particular in U.S. Pat. No. 6,358,471. Another chaining system which can be used to convey tubes in order to transport them to a whole blood analyser is described in U.S. Pat. No. 4,944,924. U.S. Pat. No. 5,582,795 also describes a tube chain which combines the tubes with a belt.

These chaining techniques are difficult to apply to automated lines, notably because they do not allow for the removal of a tube, or a tube with its support, without producing problems in the flow of tubes. Similarly, returning a tube to one of the apparatus requires the whole chain to run to the apparatus which is to be used. The chain described in the above-mentioned patents appears to be an inflexible technical solution and certainly not adapted to modern automated lines working with whole blood.

Other patents or patent applications such as U.S. Pat. No. 5,623,415, U.S. Pat. No. 4,039,288, U.S. Pat. No. 5,623,415, WO 95/03548 and WO 98/01760, describe the use of analytical equipment comprising mono-tube rails, but these appear to be intended solely for conveying tubes and do not disclose any pre-analytical means enabling the tubes to be agitated, for example, before analysis.

The category of unitary lines chiefly has the advantage that each tube can be treated as a different entity from the other tubes. To do this it requires that its own needs be met in terms of analysis, checking and additional examination, notably the possibility of easily making use of "conditioned analysis" or "reflex testing" which consists in automatically carrying out complementary examination if this can logically assist the diagnosis. This is a source of effectiveness in arriving at a diagnosis and reducing costs by doing away with any additional examinations which are irrelevant to the diagnosis.

BRIEF SUMMARY OF THE INVENTION

The invention sets out to introduce, into automated monotube lines, dedicated pre-analytical means for tubes of whole blood, enabling each whole blood analyser installed in an automatic line in unitary mode to be connected up as simply as an analyser working on blood serum or plasma.

It sets out in particular to transfer the treatment and actions carried out on the sample before it enters a whole blood analyser to the pre-analytical module for transferring it into a tube ready to be analysed in a whole blood analyser.

According to this aspect of the invention the whole blood analyser has the characteristics of an analytical terminal, the function of which is restricted to carrying out the analysis itself, like an analyser operating with plasma or whole blood, the mode of operation of which is again the unitary mode.

According to another aspect of the invention the pre-analytical module is provided for responding to demands coming from all the whole blood analysers connected to the automated line.

Advantageously, the device according to the invention comprises a pre-analytical module arranged on a mono-tube transfer line between a storage zone for the tubes to be analysed and at least one whole blood analyser operating in unitary mode, thus making it possible to combine and optimise the actions and functions needed to prepare the tubes of whole blood before they enter the analyser.

Previously, these functions and actions were carried out by the whole blood analyser or manually. The pre-analytical module makes it possible to manage these actions and functions in a logical coordinated manner with the analysers present in the automated line.

The pre-analytical module offers greater flexibility in the process of analysis by supplying agitated tubes to the whole blood analyser, but it can also supply a quality control tube for another analyser in a very short time.

The pre-analytical module also sets out to make the operations which would otherwise be manual completely automatic, while ensuring that they conform to the standardisation in force in the laboratories.

According to a first alternative embodiment the pre-analytical module comprises a device for aerating and recognising the tubes, a tube agitator for homogenising the blood before analysis, and means for automatically loading and unloading the tubes which are disposed respectively between the transfer line and the device for aerating and recognising the tubes and the tube agitator.

According to a second alternative embodiment, the pre-analytical module comprises a compartment for preserving and providing quality control tubes for analysers which require monitoring, and a tube agitator for homogenising the blood in the control tubes and in the tubes which are to be analysed, as well as means for automatically loading and unloading the tubes located respectively between the transfer line and, on the one hand, the compartment for preserving and providing the quality control tubes and, on the other hand, the tube agitator.

According to a third alternative embodiment resembling the first two, adjoining the tube agitator is a compartment for providing the analyser with quality control tubes and a device for aerating and recognising tubes and also means for automatically loading and unloading the tubes which are located respectively between the transfer line and the compartment for preserving and providing quality control tubes, the device for aerating and recognising the tubes and the tube agitator.

In a preferred embodiment, the device for aerating and recognising the tubes comprises a device for piercing the tubes thus aerating them and a reading device for recognising the information marked on the tube labels.

The compartment intended for supplying the analyser with quality control tubes comprises an insulating container the interior of which is kept at constant temperature by a regulating module and a switching device for transferring the regulating parameters via a network interface module in order to allow a control and feedback module to receive instructions from a telemaintenance centre or an internet or intranet type information network.

According to a preferred embodiment the regulating module is a regulating module of the known Peltier-effect kind.

According to another advantageous feature, the transfer line is folded on itself so as to form an ascending track and a descending track and is coupled to a tube exchanger/loader disposed between the pre-analytical module and the analyser which enables the tubes either to be transferred from one track to the other or to overtake the tube in front of them on the same track.

In this embodiment the tube exchanger/loader device separates each of the two tracks into two sections and is made up of a drawer divided into four compartments, the drawer being movable in translation in a direction perpendicular to the longitudinal axis of the conveying rail. In this way it is possible for a tube to be transferred from one track to the other by positioning the compartment which contains it between the two sections of the other track.

The movement of a tube in front of another one on the same track is achieved by positioning the compartment containing the tube which is to be overtaken outside its track, thus enabling the tube behind it on the same track to occupy the adjacent compartment, in a first stage, before continuing its progress on the same track, in a second stage.

To allow automatic loading/unloading of the tubes between the conveying line and the pre-analytical module, the conveying line is divided up into sections consisting of conveyor belts separated from one another by loading/unloading devices in the form of drawers divided into compartments limited by two partitions arranged parallel to the longitudinal direction XX' of the conveying rail and of such dimensions as to accommodate a tube and its support in each case.

In a preferred embodiment the loading and unloading devices in the form of a drawer are divided into three compartments, an end compartment for loading and unloading the tubes in the pre-analytical module and two compartments dedicated to transferring tubes between the two adjacent sections of the ascending track and descending track, respectively.

In order to achieve an optimum operating rate for the agitator and comply with the conditions set down by the NCCLS for use in laboratories, the agitator comprises a wheel provided with a specified number of indentations each capable of accommodating a tube, each tube to be agitated being loaded into an indentation by a loading device.

Finally, to allow automatic loading of the tubes from the storage zone onto the transfer line, the storage zone comprises a manipulating arm which assigns each tube on a conveyor to a support. The tubes with their supports are then transported by the conveyor along the conveying line.

It is advantageous if the pre-analytical module comprises, in addition to the tube agitator, a detector for detecting the level of liquid contained in a tube.

The pre-analytical module may also comprise in addition to the tube agitator a heating means for heating the tubes on the tube agitator by the Peltier effect.

The preserving compartment mentioned above may also contain tubes intended for analysis. The pre-analytical module may also comprise several storage compartments intended for quality control tubes or tubes intended for analysis.

According to yet another feature of the invention the pre-analytical module comprises a detector for detecting the presence of clots in the tubes of blood. This detector preferably comprises optical means or sound waves or electrical means.

BRIEF DESCRIPTION OF THE DRAWINGS

In the description that follows which is provided solely by way of example, reference is made to accompanying drawings, wherein.

DETAILED DESCRIPTION OF THE INVENTION

Figure 1:
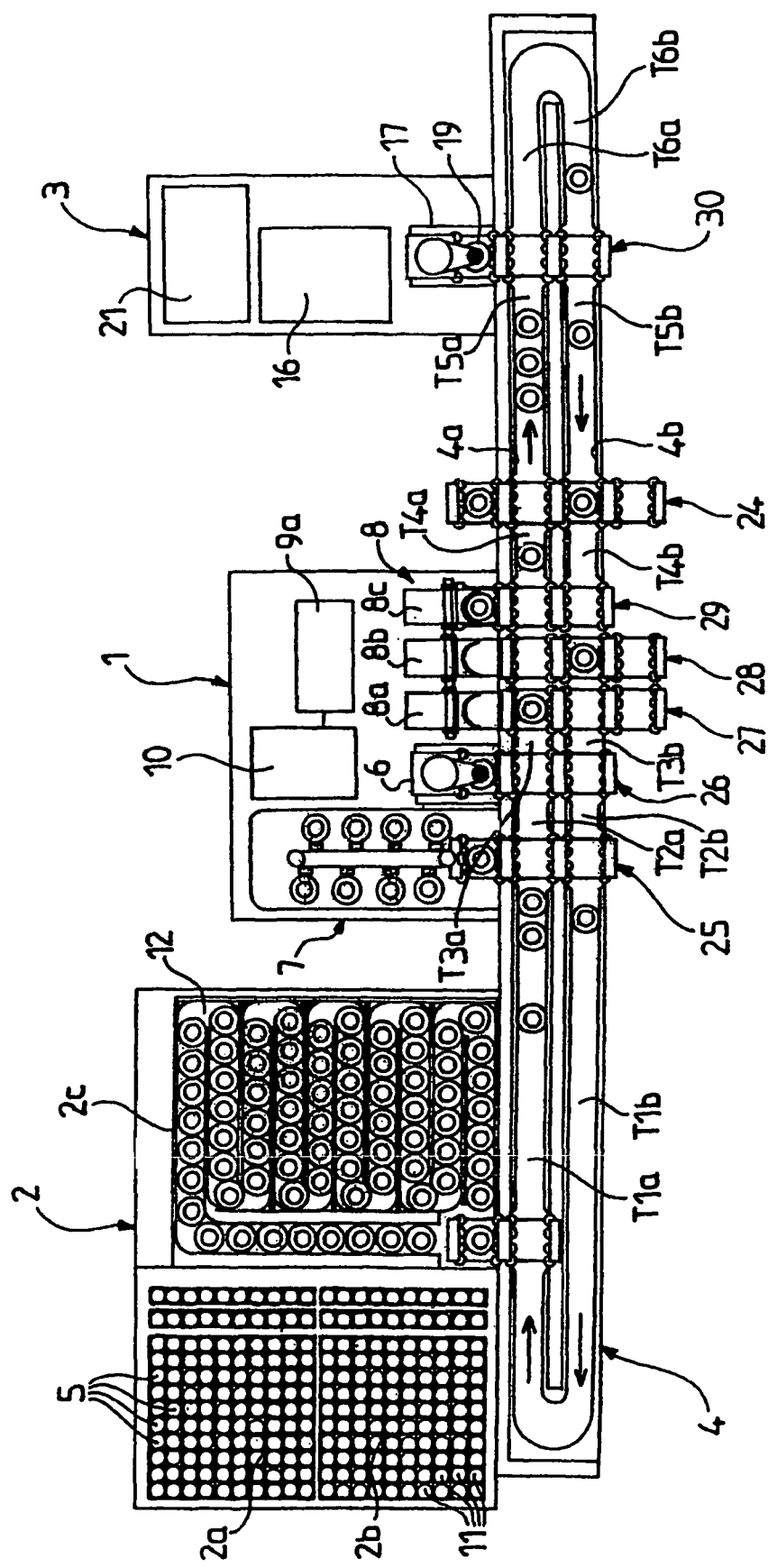
FIG. 1 is a plan view of an embodiment of a device according to the invention which allows tubes of blood to be supplied automatically to a mono-tube whole blood analyser.
Figure 2:
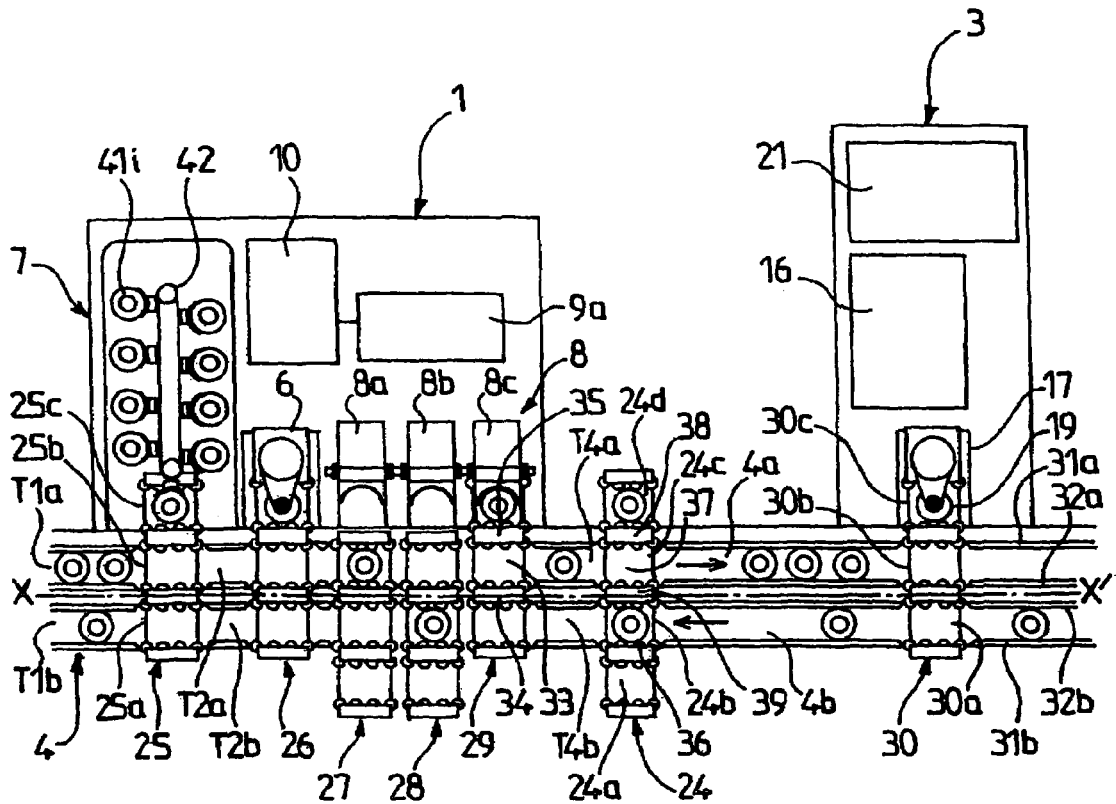
FIG. 2 shows part of the device of FIG. 1 on an enlarged scale.
Figure 3:
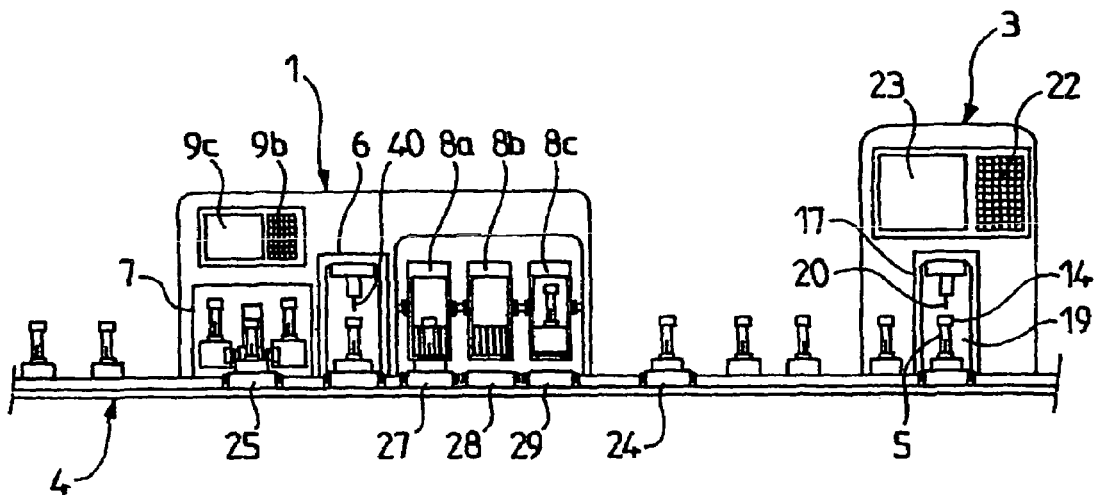
FIG. 3 is a front view corresponding to FIG. 2.

Reference will be made first of all to FIGS. 1 to 3 in which corresponding elements have been given the same reference numerals and which show a first embodiment of a device according to the invention. This device comprises a pre-analytical module 1 arranged between a storage zone 2 for the tubes of blood to be analysed and at least one mono-tube analyser 3. A mono-tube conveying line 4 in the form of a rail transports the tubes 5 from the storage zone 2 to their destination, either from the pre-analytical module 1 or from one or more mono-tube analysers 3. By the term "mono-tube" is meant that the operation in question (conveying, analysis, etc.) is carried out on an individual tube and not on a plurality of tubes.

The pre-analytical module 1 is intended to perform a certain number of operations prior to a subsequent analysis. It is made up of a device 6 for aerating and recognising tubes 5, a compartment 7 for storing and providing quality control tubes, and an agitator 8 which, in the embodiment shown, allows the tubes to be agitated simultaneously by means of three wheels 8a, 8b and 8c rotatably mounted about a horizontal axis. The storage compartment 7 may also contain tubes 5 intended for analysis.

The pre-analytical module 1 also comprises a control and feedback module 9a (FIGS. 1 and 2) coupled to a keyboard 9b and a display screen 9c (FIG. 3). The latter make it possible to monitor and observe the operation of the elements that make up the pre-analytical module 1. The control and feedback module 9a is furthermore coupled to a network interface module 10 enabling the control and feedback module 9a to receive instructions from a telemaintenance centre (not shown) through an internet or intranet type information network, for example.

Figure 4:
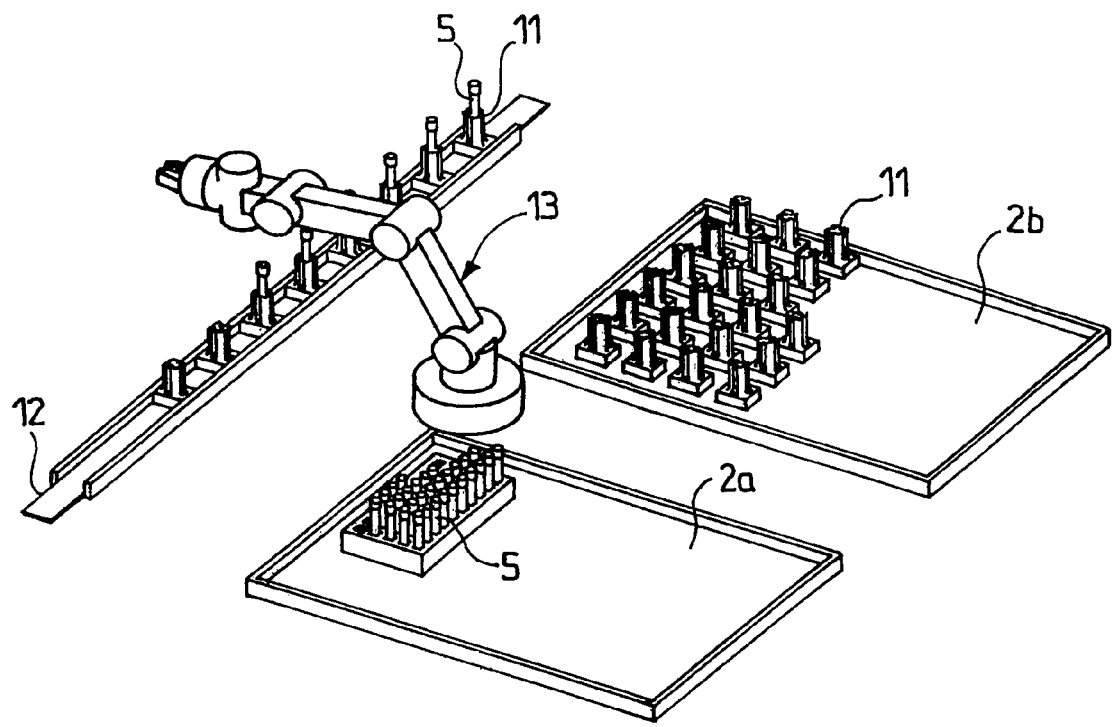
FIG. 4 is a perspective view of a robot arm for gripping the tubes between the storage zone and the transfer line provided in the device shown in FIGS. 1 and 2.

The storage zone 2 (FIG. 1) comprises a zone 2a for storing the tubes 5 which are to be analysed, a zone 2b for storing supports 11 for tubes 5 and an assembly zone 2c intended for assembling the tubes 5 which are to be analysed on their supports 11 and enabling the tubes which are to be analysed to be transported with their supports on a conveyor 12 folded in a zigzag configuration towards the conveying rail 4. The combining of the tubes 5 with their supports 11 is carried out as shown in FIG. 4, using a robot manipulating arm 13 which assigns a tube 5 to be analysed, which is located in the storage zone 2a for the tubes, to a support 11 in the storage zone 2b for the supports, on the conveyor 12 in the assembly zone 2c.

Figures 5, 6:
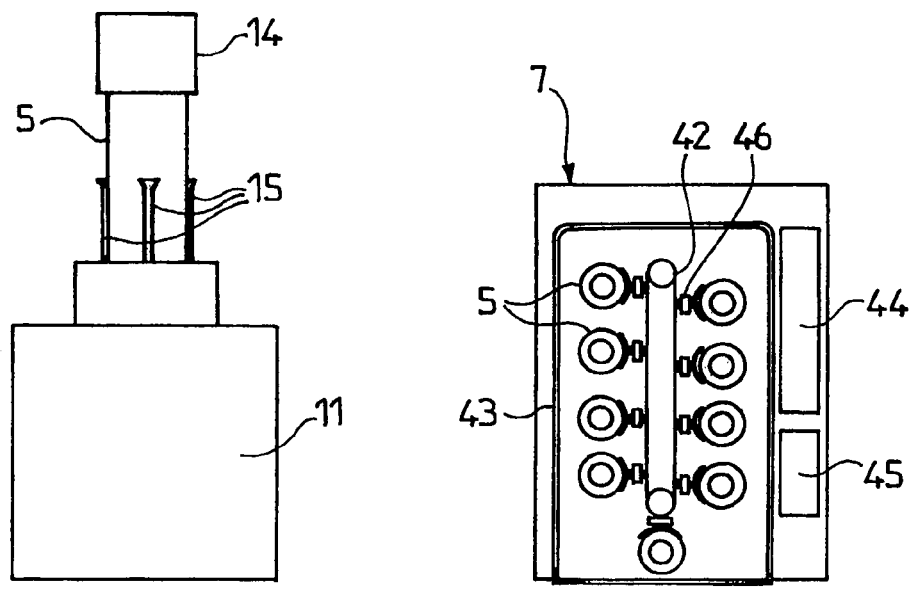
FIG. 5 is a view showing an embodiment of a tube support member fitted to the transfer line in FIGS. 1 to 3.
FIG. 6 is an embodiment of the preserving compartment provided on the device in FIGS. 1 to 3.

As shown in FIG. 5, the tubes 5 are provided with individual stoppers 14 and are placed vertically inside a support 11 where they are held by spring plates 15.

The analyser 3 comprises, in known manner, a blood analysing device 16 coupled with sampling means 17 comprising an indentation 19 for holding each tube 5 which is to be analysed in alignment with a sampling needle 20. The analyser 3 also comprises means 21 for controlling the analysing device, coupled with a keyboard 22 and a monitoring screen 23.

Advantageously, the mono-tube conveying line 4 is folded on itself so as to form two parallel tracks 4a, 4b moving in opposite directions to one another and comprises a tube exchanging/loading device 24 disposed across the two tracks 4a and 4b in order to allow tubes to be transferred between the two tracks or to enable a tube on one track to overtake the tube in front of it on the same track.

The first track 4a, hereinafter referred to as the ascending track, moves the tubes 5 from the storage zone 2c towards the analyser 3 and the second track 4b, or descending track, moves them in the opposite direction between the analyser and the storage zone 2.

To allow the tubes mounted on their supports to be loaded onto the conveying rail or to be unloaded into the different modules that make up the pre-analytical module 1 and in the analyser 3, the conveying line 4 is divided up into sections designated T1a to T6a on the first track 4a and T1b to T6b on the second track 4b, separated from one another by loading/unloading devices designated 25 to 30 in the form of drawers divided into compartments 25a, 25b, 25c; . . . ; 30a, 30b, 30c.

Each section 25a, 25b, 25c; . . . ; 30a, 30b, 30c of the conveying line 4 is in the form of a conveyor belt moving between two side walls 31a, 32a; 31b, 32b, respectively. The compartments 25a, 25b, 25c; . . . ; 30a, 30b, 30c of each of the loading/unloading devices are aligned in a direction perpendicular to the longitudinal axis XX' of the conveying rail 4 and are dimensioned so as to each accommodate a tube 5 and its support 11 coming from the section of rail adjacent thereto.

To allow a tube 5 with its support 11 to fit into a compartment, each compartment has a base 33 located in the same plane as that of the two conveyor belts belonging to the two sections of rail adjacent thereto and limited by two partitions 34, 35 perpendicular to said base 33 and aligned respectively with the side walls 31 and 32 which delimit the conveyor belts of sections T1a to T6a and T1b to T6b of the conveying line 4. The movement of the tube supports 11 in the compartment is ensured by drive rollers 36 in contact with the tube supports 11.

The tube exchanger/loader 24 is also in the form of a drawer which is movable in translation in a direction perpendicular to the longitudinal axis XX' of the conveying rail 4. Unlike the loading/unloading devices, it is made up of four compartments 24a, 24b, 24c, 24d comprising, in a similar manner to those of the loading/unloading device, a base 37 bounded by two partitions 38, 39 perpendicular to the base 37 and extending in the direction of the longitudinal axis XX' of the conveying line 4. The transfer of a tube 5 from one track to the other is effected by moving the tube exchanger/loader device 24 in the direction perpendicular to the longitudinal axis XX' of the conveying rail 4, aligning the partitions of the compartment containing the tube from a track which is to be transferred respectively with the side walls 31 and 32 of the other track. This manoeuvre, which takes place under the control of the control and feedback device 9, makes it possible to reverse the direction of travel of a tube 5 and its support 11 on the conveying rail 4. However, it is also possible to move a tube 5 and its support 11 outside the track on which they are travelling by placing the tube 5 and its support 11 in a compartment 24a, 24d, respectively, located at one end of the drawer in order to allow the tube and its support travelling behind it on the same track to move into the respectively adjacent compartment 24b, 24c in order to overtake them on the same track.

The tube aerating and recognising device 6 and the compartment 7 are supplied with tubes by the mono-tube conveying line 4 using the loading/unloading devices 25 and 26.

The loading/unloading device 26 makes it possible either to transfer tubes continuously onto each of the tracks 4a, 4b, without going via the tube aerating and recognising device 6, or to pick up a tube 5 from the track 4a in order to transfer it into the tube aerating and recognising device, in a position enabling it to be pierced by a piercing device 40 (FIG. 3) for aerating it and enabling its marking to be recognised by the reading of the data characterising it, marked on a label attached to the tube 5, by a suitable reader (not shown). This information tells the analyser, in particular, what kind of analysis and what kind of action it has to carry out on the contents of each tube. Once the tube has been aerated and identified it is brought along on the conveying rail 4 to be steered either to the agitator 8 or directly to the analyser 3.

The compartment 7 which is intended for storing and managing control bloods, contains a specified number of tube emplacements 41i (FIG. 2) arranged on a belt 42 which supplies the conveying rail 4 via the loading/unloading device 25 to allow either continuous transfer of the tubes onto each of the tracks 4a, 4b or in order to pick up a tube from the belt 42 to transfer it to the track 4a of the conveying rail or vice versa in order to pick up a tube from one of the tracks 4a, 4b of the conveying rail to transfer it into a free emplacement 41i on the belt 42.

In the embodiment shown in FIG. 6, the compartment 7 has an insulating container 43 the interior of which is kept at a constant temperature by a regulating module 44 of the known kind operating by the Peltier effect, for example. It also comprises a switching device 45 for transferring the regulating parameters to the network interface module 10 in FIGS. 1 and 2. The tubes 5 are held on the belt 42 by mechanical or magnetic fixing means 46 controlled by the control and feedback device 9.

In the configuration in FIGS. 1 to 3, the agitator 8 agitates three tubes simultaneously by means of the indentations in three wheels 8a, 8b, 8c which are respectively supplied by three loading/unloading devices 27, 28, 29. However, this number may equally well be reduced as increased as a function of, on the one hand, the capacity of the analyser or analysers to be served and, on the other hand, taking account of the minimum agitation time for the tubes which is needed to re-suspend the blood cells for analysis in each tube to a satisfactory extent.

Figure 8:
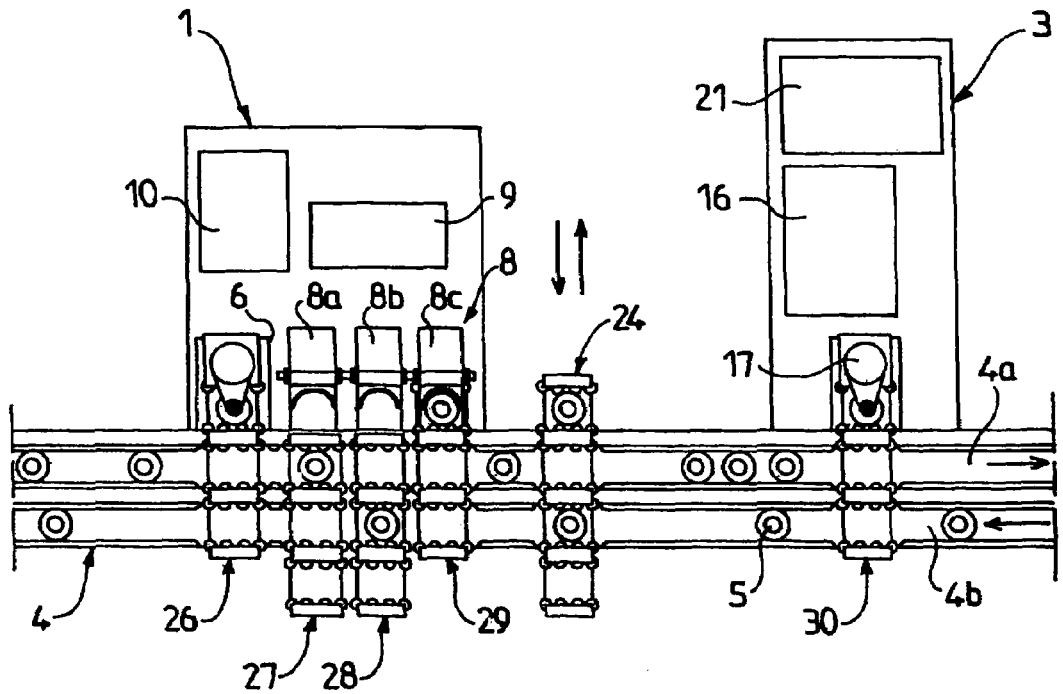
FIGS. 7 and 8 are two view showing two alternative embodiments of a device according to the invention.
Figure 7:
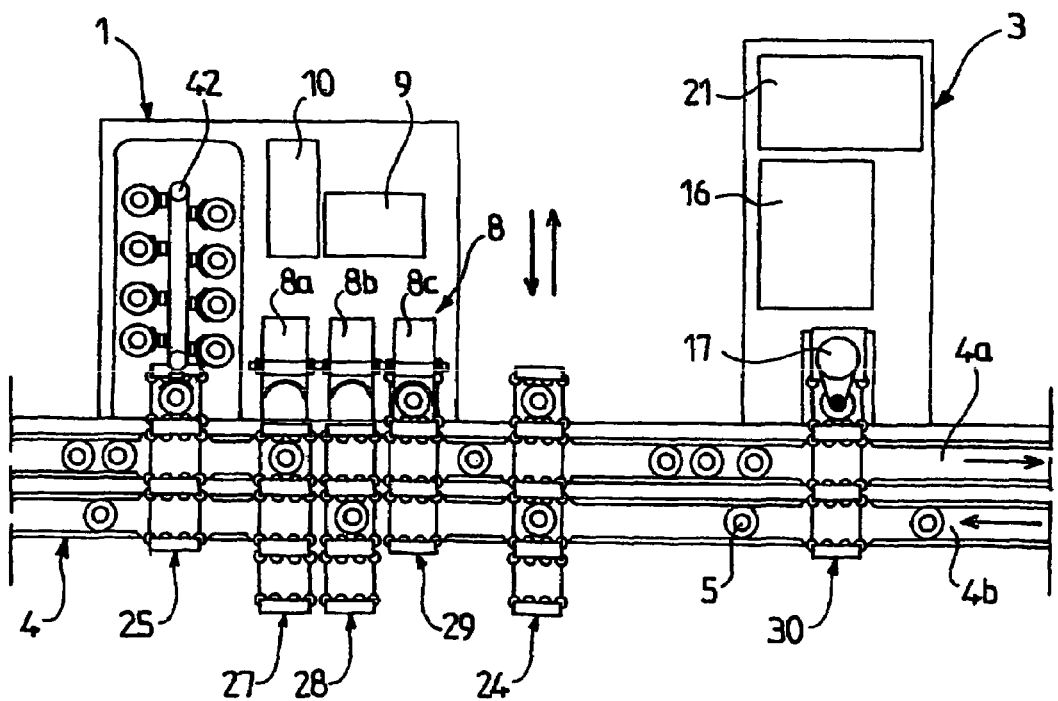

The exemplary embodiments of the device according to the invention shown in FIGS. 7 and 8 show the different versions of the embodiment in FIGS. 1 to 3. In the second alternative embodiment of the device shown in FIG. 7 in which the elements corresponding to those in FIGS. 1 to 3 bear the same reference numerals, the pre-analytical module 1 has the same elements as in FIGS. 1 to 3 but without the device 6 for aerating and recognising the tubes. This more simplified system is more particularly suitable for carrying out control operations on the analysers.

According to the third alternative embodiment of the invention shown in FIG. 8, in which elements corresponding to those in FIGS. 1 and 2 bear the same reference numerals, the pre-analytical module is formed solely by a device 6 for aerating and recognising the tubes and a module 8 for agitating the tubes in order to homogenise the blood and prevent clotting.

Figure 9:
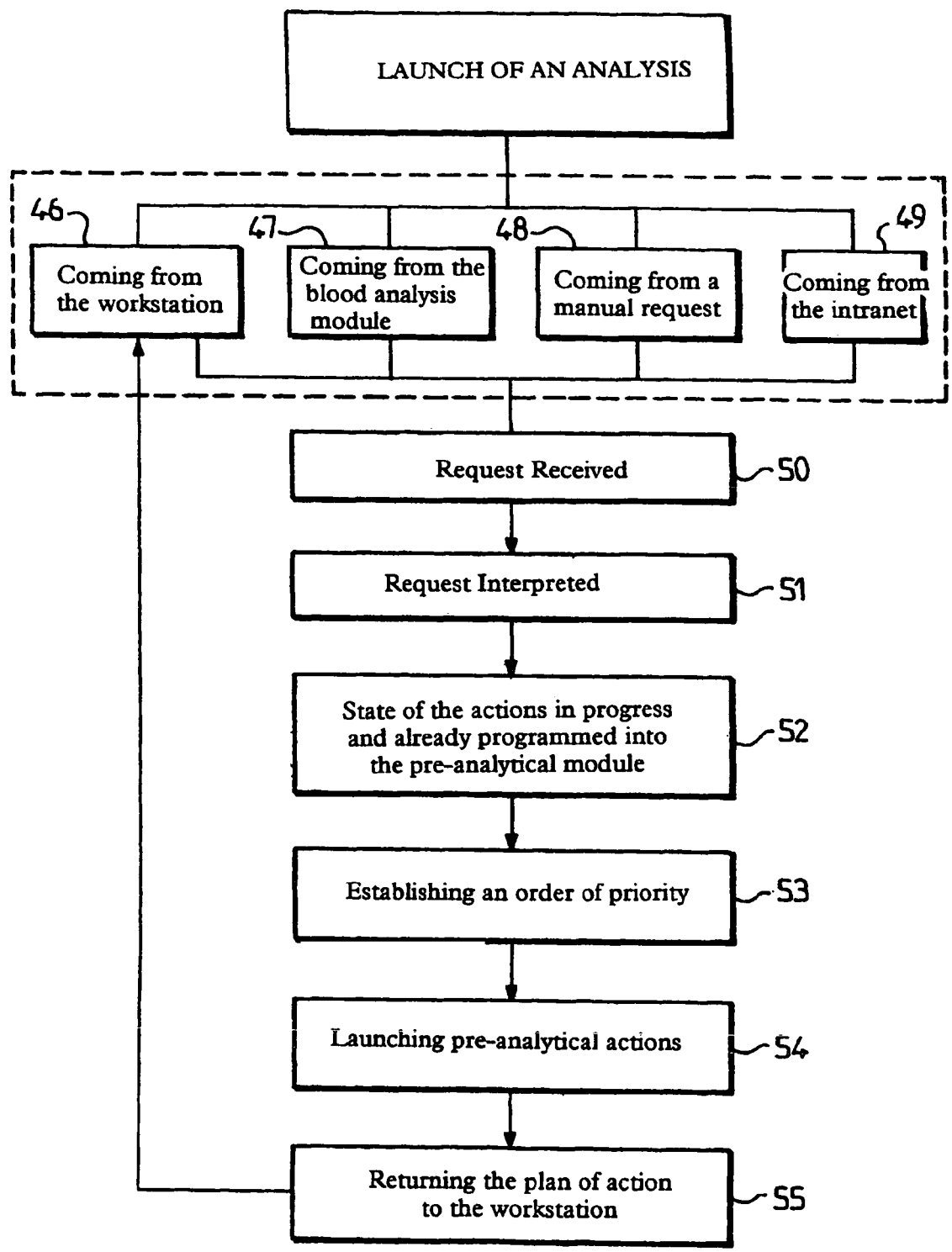
FIG. 9 is a flow chart illustrating a method of operation of a device according to the invention.

FIG. 9 describes a method of operation of the pre-analytical module 1 starting from a request for analysis which may come from four different users. In the example shown the request may come from a workstation 46, a whole blood analysing module 47 which is present or connected to the automated line 4, a manual request 48 sent by an operator using the interface of the pre-analytical module 1 wishing to undertake maintenance action, for example, and finally a request 49 coming from the network through the intranet or internet of a telemaintenance centre to initialise the launch of quality control, for example.

When a request is received at step 50 by the pre-analytical module 1 it is interpreted at step 51 in order to verify the validity of the request. Then in step 52 a record of the actions programmed and taking place is drawn up in order to check that the pre-analytical module 1 actually has the capacity to deal with the new request within a specified period. Once the analysis is complete and if the conditions of acceptance of the new request have been met the pre-analytical module integrates the new request in its planning, in step 53, in accordance with its priorities. Then the pre-analytical module continues to execute the requests, taking account of its new plan updated by accepting the new request to launch pre-analytical actions in step 54. Next, the pre-analytical module 1 reports in step 55 its new state to the issuer of the request.

Figure 10:
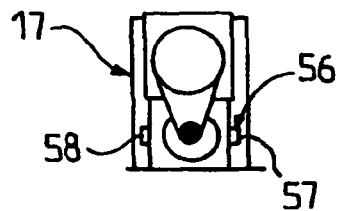
FIGS. 10 and 11 are a plan view and front view of a liquid level detector.
Figure 11:
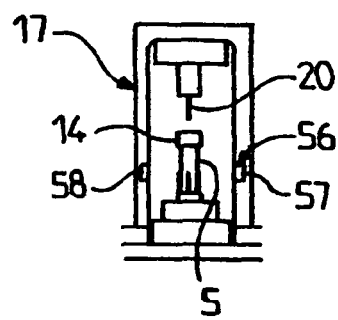

In the embodiment shown in FIGS. 10 and 11, the pre-analytical module comprises, in addition to the tube agitator, a detector 56 designed to detect the level of a liquid contained in a tube 5. In the example this detector 56 is combined with sampling means 17 analogous to those described previously. The detector 56 comprises an emitter 57 designed to emit a light wave and a receptor 58 designed to receive the light wave which has passed through the tube, thereby determining the level of liquid contained in the tube.

Figure 12:
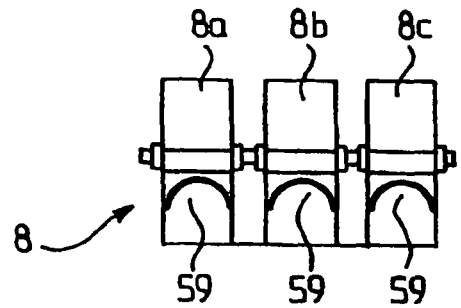
FIG. 12 is a front view of a tube agitator provided with a Peltier-effect heating member.

FIG. 12 shows a tube agitator 8 comprising three wheels 8a, 8b and 8c, each of which carries a heater 59 for heating the tubes 5 on the tube agitator. In the embodiment shown the heaters 59 are each made in the form of a plate operating by the Peltier effect.

Figure 14:
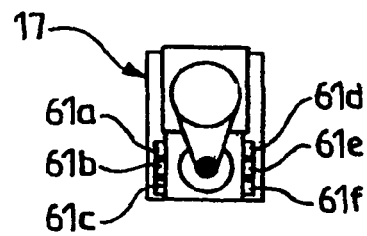
FIGS. 14 and 15 are a plan view and a front view of a detector intended to identify the presence of clots inside a tube.
Figure 13:
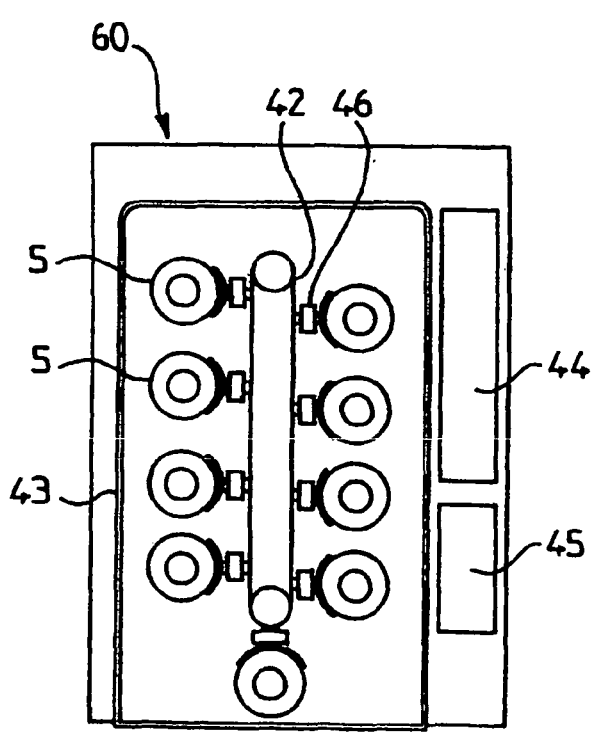
FIG. 13 is a plan view of a storage compartment analogous to that in FIG. 6 intended for quality control tubes or tubes intended for analysis.
Figure 15:
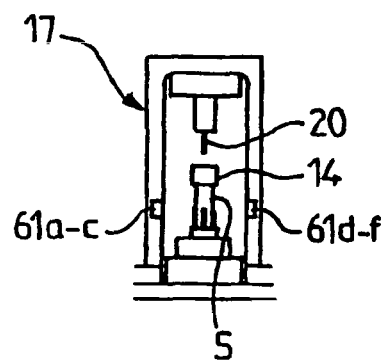

FIG. 13 shows a storage compartment 60 analogous to the one described previously with reference to FIG. 6, but the insulating container 43 of the compartment is provided in this case to accommodate the tubes 5 intended for analysis. Generally speaking, the pre-analytical module 1 may comprise several storage compartments 7 or 60 intended for quality control tubes or for tubes which are intended for analysis. In the embodiments shown in FIGS. 14 and 15, the pre-analytical module comprises detectors 61a, 61b, 61c, 61d, 61e and 61f arranged to detect the presence of clots in the tubes of blood 5. These six detectors may comprise optical means or sound waves or electrical means.

The invention claimed is:

1. An analyzing system, comprising:
   at least one whole blood analyzer operating in a unitary mode;
   a storage zone for tubes to be analyzed;
   a mono-tube transfer line for transferring tubes between the storage zone and the at least one whole blood analyzer operating in a unitary mode;
   a pre-analytical module comprising;
      at least one tube agitator for homogenizing the blood before analysis, a device for aerating and recognizing the tubes comprising a device for reading label information on the tubes, the pre-analytical module being disposed on the mono-tube transfer line between the storage zone for tubes to be analyzed and the at least one whole blood analyzer; and
   a plurality of means for automatically loading and unloading the tubes, one of the plurality of means for automatically loading and unloading the tubes disposed between the tube agitator and the mono-tube transfer line, one of the other plurality of means for automatically loading and unloading the tubes disposed between the device for aerating and recognizing the tubes and the mono-tube transfer line.

2. The analyzing system according to claim 1, wherein the device for aerating and recognizing the tubes further comprises a device for piercing the tubes which enables tubes to be aerated.

3. The analyzing system according to claim 1, wherein the pre-analytical module further comprises a compartment for storing and providing quality control tubes for use in tests on whole blood analyzers and one of the other plurality of means for automatically loading and unloaded the tubes disposed between the mono-tube transfer line and the compartment for storing and providing the quality control tubes.

4. The analyzing system according to claim 3, wherein the compartment for storing and providing the quality control tubes comprises an insulating enclosure with an interior kept at a constant temperature by a regulating module and a switching device for transferring regulating parameters of the regulating module to a network interface module.

5. The analyzing system according to claim 4, wherein the quality control tubes are fixed inside the insulating enclosure on a belt by mechanical or magnetic fixing means controlled by a control and feedback device.

6. The analyzing system according to claim 4, wherein the regulating module is a Peltier effect regulating module.

7. The analyzing system according to claim 3, wherein the pre-analytical module further comprises a number of storage compartments configured for quality control tubes or tubes for analysis.

8. The analyzing system according to claim 3, wherein the pre-analytical module further comprises a detector for detecting presence of clots in tubes of blood.

9. The analyzing system according to claim 8, wherein the detector comprises optical means or sound waves or electrical means.

10. The analyzing system according to claim 1, wherein the tube agitator comprises a wheel provided with a specified number of indentations each configured to receive a tube, each tube which is to be agitated being loaded into an indentation by the means for automatically loading and unloading the tubes.

11. The analyzing system according to claim 1, wherein the pre-analytical module comprises a network interface module enabling a control and feedback module to receive instructions from a telemaintenance center or from an internet or intranet information network.

12. The analyzing system according to claim 1, wherein the storage zone comprises a manipulating arm for associating on a conveyor each tube with a support, and wherein the conveyor transports the tubes with their supports on the conveying line.

13. The analyzing system according to claim 1, wherein the whole blood analyzer comprises a blood analyzing device coupled with sampling means comprising an indentation for holding each tube which is to be analyzed vertically in alignment with a sampling needle.

14. The analyzing system according to claim 1, wherein the pre-analytical module further comprises a detector for detecting a level of a liquid contained in a tube.

15. The analyzing system according to claim 1, wherein the pre-analytical module further comprises a heater for heating the tubes on the tube agitator by a Peltier effect.

* * * * *